United States Patent
Mann

(10) Patent No.: US 11,324,637 B2
(45) Date of Patent: May 10, 2022

(54) EARPLUG

(71) Applicant: Vibes LLC, Minneapolis, MN (US)

(72) Inventor: Jackson Robert Mann, Minneapolis, MN (US)

(73) Assignee: Vibes LLC, Wayzata, MN (US)

( * ) Notice: Subject to any disclaimer, the term of this patent is extended or adjusted under 35 U.S.C. 154(b) by 603 days.

(21) Appl. No.: 15/344,920

(22) Filed: Nov. 7, 2016

(65) Prior Publication Data

US 2017/0128268 A1 May 11, 2017

Related U.S. Application Data

(60) Provisional application No. 62/252,423, filed on Nov. 7, 2015.

(51) Int. Cl.
| | | |
|---|---|---|
| *A61F 11/06* | (2006.01) | |
| *A61F 11/00* | (2022.01) | |
| *A61F 11/08* | (2006.01) | |

(52) U.S. Cl.
CPC ............ *A61F 11/08* (2013.01); *A61F 11/085* (2022.01)

(58) Field of Classification Search
CPC .......... A61F 11/06; A61F 11/08; A61F 11/10; A61F 11/12; A61F 2011/085; H04R 1/10; H04R 1/1016
USPC .................. 128/864, 865, 866, 867; 381/328
See application file for complete search history.

(56) References Cited

U.S. PATENT DOCUMENTS

| | | | | |
|---|---|---|---|---|
| 2,430,229 A | * | 11/1947 | Kelsey ............... | H04R 1/1058 381/338 |
| 2,619,960 A | * | 12/1952 | Reynolds ............... | A61F 11/08 128/868 |
| 3,930,560 A | | 1/1976 | Carlson et al. | |
| 4,852,683 A | * | 8/1989 | Killion ................. | A61F 11/10 181/130 |
| 5,113,967 A | * | 5/1992 | Killion ................. | A61F 11/08 181/132 |
| 5,631,965 A | * | 5/1997 | Chang ................. | A61F 11/08 381/72 |
| D402,752 S | | 12/1998 | Falco | |
| D419,676 S | | 1/2000 | Garcia | |
| D618,209 S | | 6/2010 | Andre et al. | |
| D618,210 S | | 6/2010 | Andre et al. | |
| D624,901 S | | 10/2010 | Blanchard | |
| D649,656 S | | 11/2011 | Petersen | |
| D675,194 S | | 1/2013 | Andre et al. | |
| 2005/0094835 A1 | * | 5/2005 | Doty ................... | A61F 11/08 381/328 |
| 2006/0081415 A1 | | 4/2006 | Knauer et al. | |

(Continued)

*Primary Examiner* — Victoria Hicks Fisher
(74) *Attorney, Agent, or Firm* — Mueting Raasch Group

(57) ABSTRACT

An earplug extending along an earplug axis may include an outer portion and an inner portion. The outer portion may include a proximal portion extending from a second end region, a distal portion extending from a first end region, and a slant portion therebetween. The outer portion may define an interior space. The inner portion may extend between a first and second end region and may be coupled to the outer portion within the interior space. A distance between an end of the inner portion proximate the second end region of the inner portion and an end of the outer portion proximate the second end region of the outer portion may be greater than a length of the proximal portion of the outer portion measured along the earplug axis.

17 Claims, 8 Drawing Sheets

(56) References Cited

U.S. PATENT DOCUMENTS

| | | |
|---|---|---|
| 2008/0207790 A1 | 8/2008 | Knauer et al. |
| 2009/0234182 A1 | 9/2009 | Buchholz |
| 2013/0294634 A1* | 11/2013 | Chen ............... H04R 1/1066 381/380 |
| 2014/0014121 A1 | 1/2014 | Endle et al. |
| 2014/0301591 A1* | 10/2014 | Yang ............... H04R 1/1016 381/380 |
| 2015/0047650 A1 | 2/2015 | Blanchard |

\* cited by examiner ical relationships that may help to achieve this desirable dampening
EARPLUG

CROSS-REFERENCE TO RELATED APPLICATIONS

This application claims benefit of U.S. Provisional Application No. 62/252,423, filed Nov. 7, 2015, and entitled "Earplug," which is incorporated herein in its entirety.

FIELD OF THE DISCLOSURE

The disclosure herein relates to earplugs. More particularly, the disclosure relates to sound filtering earplugs for use in dampening various frequencies of sound.

SUMMARY

Exemplary earplugs for dampening sound waves are described herein. The exemplary earplugs may be used for attenuating multiple frequencies of sound in a level way (e.g., flattening) such that overall sound quality may not be distorted by passing through the earplug. The exemplary earplugs described herein provide various dimensional relationships that may help to achieve this desirable dampening of various frequencies of sound in level way.

An exemplary earplug extending along an earplug axis may include an outer portion and an inner portion. The outer portion may extend between a first end region and a second end region. The outer portion may include a proximal portion extending from the second end region of the outer portion, a distal portion extending from the first end region of the outer portion, and a slant portion between the proximal portion and the distal portion. The outer portion may define an interior space and an opening at the second end region extending into the interior space. The inner portion may extend between a first end region and a second end region. At least a portion of the inner portion may be coupled to the outer portion and located within the interior space of the outer portion. The inner portion may define an aperture extending between the first end region of the inner portion and the second end region of the inner portion. A distance between an end of the inner portion proximate the second end region of the inner portion and an end of the outer portion proximate the second end region of the outer portion may be greater than a length of the proximal portion of the outer portion measured along the earplug axis.

In one or more embodiments, the length of the proximal portion of the outer portion may be less than a diameter of the aperture of the inner portion measured perpendicular to the earplug axis. In one or more embodiments, the length of the proximal portion of the outer portion may be less than half of a length of the distal portion of the outer portion measured along the earplug axis. In one or more embodiments, the distance between the end of the inner portion proximate the second end region of the inner portion and the end of the outer portion proximate the second end region of the outer portion may be greater than a quarter of the length of the distal portion of the outer portion measured along the earplug axis.

In one or more embodiments, the length of the proximal portion of the outer portion and a length of the slant portion of the outer portion measured along the earplug axis combined may be less than a length of the distal portion of the outer portion measured along the earplug axis. In one or more embodiments, the earplug may also include a filter portion located in the aperture of the inner portion. In one or more embodiments, the length of the proximal portion of the outer portion may be less than a length of the filter portion measured along the earplug axis.

In one or more embodiments, the earplug may further include an eartip portion removably coupled to the second end region of the inner portion and configured to be positioned in an ear canal. The eartip portion may extend between a first end region and a second end region and defines an interior space. At least a portion of the second end region of the inner portion may extend within the interior space of the eartip portion at the first end region of the eartip portion. In one or more embodiments, at least a portion of the second end region of the outer portion may extend within the interior space of the eartip portion at the first end region of the eartip portion. In one or more embodiments, the proximal portion of the outer portion may define a diameter greater than a diameter of the distal portion of the outer portion. The diameters of the proximal portion and distal portion may be measured perpendicular to the earplug axis. In one or more embodiments, the slant portion may define a varying diameter extending between the proximal portion and the distal portion. The diameter of the slant portion may be measured perpendicular to the earplug axis.

Another exemplary earplug may include an outer portion, an inner portion, a filter portion, and an eartip portion. The outer portion may extend between a first end region and a second end region. The outer portion may define an interior space and an opening at the second end region extending into the interior space. The inner portion may extend between a first end region and a second end region. At least a portion of the inner portion may be coupled to the outer portion and located within the interior space of the outer portion. The inner portion may define an aperture extending between the first end region of the inner portion and the second end region of the inner portion. The filter portion may be located in the aperture of the inner portion. The eartip portion may be removably coupled to the second end region of the inner portion and may be configured to be positioned in an ear canal. The eartip portion may extend between a first end region and a second end region and may define an interior space. At least a portion of the second end region of the inner portion may extend within the interior space of the eartip portion at the first end region of the eartip portion. At least a portion of the second end region of the outer portion may extend within the interior space of the eartip portion at the first end region of the eartip portion.

In one or more embodiments, an end of the outer portion proximate the second end region of the outer portion may be closer to the first end region of the eartip portion than the second end region of the eartip portion. In one or more embodiments, the eartip portion may contact an outer surface of the outer portion. In one or more embodiments, the filter portion may be located at the second end region of the inner portion.

In one or more embodiments, the interior space of the eartip portion may define a passage extending between the first end region of the eartip portion and the second end region of the eartip portion. At least a portion of the inner portion may extend within at least a portion of the passage of the eartip portion. In one or more embodiments, a diameter of the passage of the eartip portion proximate the second end region of the eartip portion may be less than a diameter of the at least a portion of the passage that receives the inner portion. The inner portion may define a diameter such that the inner portion may be restricted from passing through the passage of the eartip portion proximate the second end region of the eartip portion. A distance between the second end region of the inner portion and the second end region of the eartip portion may be greater than a distance that the outer portion extends within the interior space of the eartip portion.

Yet another exemplary earplug may include an outer portion, an inner portion, a filter portion, and an eartip portion. The outer portion may extend between a first end region and a second end region. The outer portion may define an opening at the second end region of the outer portion and an interior space. The inner portion may extend between a first end region and a second end region. At least a portion of the inner portion may be coupled to the outer portion and located within the interior space of the outer portion. The inner portion may define an aperture extending between the first end region of the inner portion and the second end region of the inner portion. The filter portion may be located in the aperture of the inner portion. The eartip portion may be removably coupled to the second end region of the inner portion and may be configured to be positioned in an ear canal. The eartip portion may extend between a first end region and a second end region and may define an interior space. An end of the inner portion proximate the second end region of the inner portion may be closer to the second end region of the eartip portion than the first end region of the eartip portion.

DETAILED DESCRIPTION OF EXEMPLARY EMBODIMENTS

Figure 1:
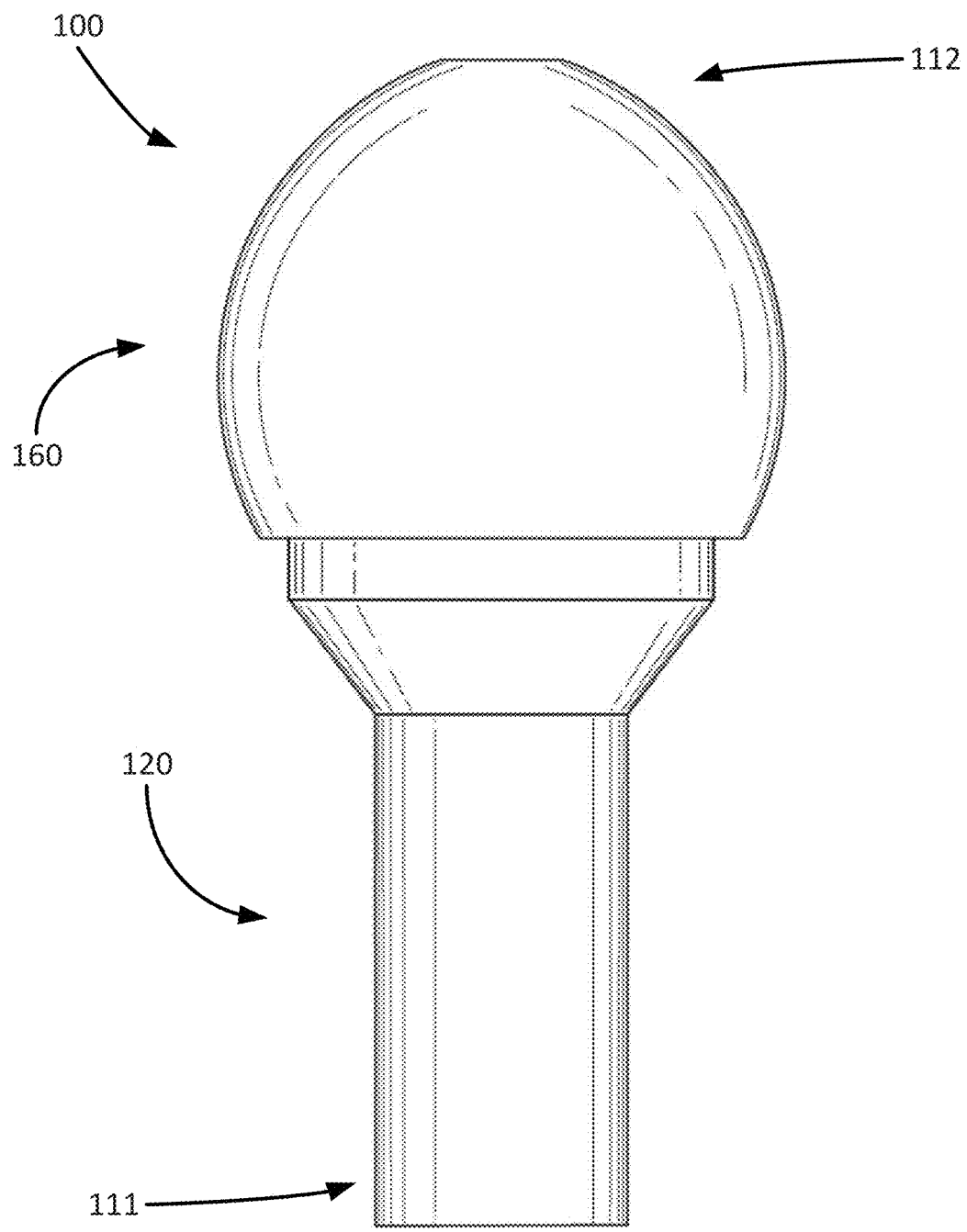
FIG. 1 is a front view of an exemplary earplug.

The exemplary earplugs 100 described herein may include an inner portion 140, an outer portion 120, a filter portion 180, and an eartip portion 160. As shown in FIG. 1, an exemplary earplug 100 may extend from a proximal end region 112 to distal end region 111. The proximal end region 112 of the earplug 100 may be configured to be inserted into an ear canal of human ear, and once inserted, may be configured to attenuate, or damp, various frequencies of sound from entering into a user's ear canal (e.g., to protect a user's ear from damage from sound). Furthermore, the earplug 100 may be configured to dampen sound waves entering the ear canal such that multiple frequencies are attenuated equally. In other words, an equal attenuation across multiple frequencies may maintain sound quality and integrity while reducing the decibel level.

Figure 4:
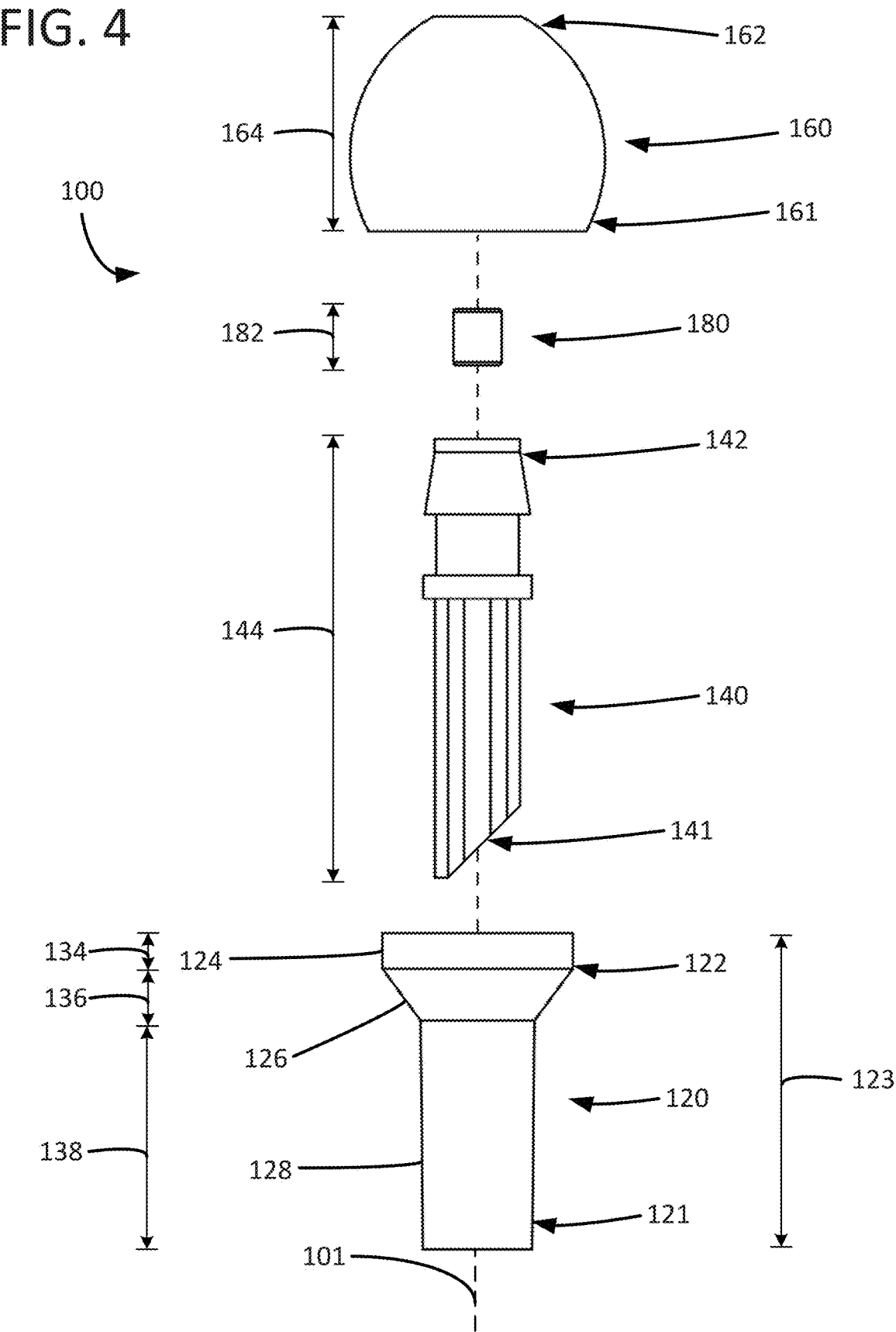
FIG. 4 is an exploded front view of the earplug of FIGS. 1-3.

The exterior of the earplug 100 as shown in FIG. 1 may only show the eartip portion 160 located proximate the proximal end region 112 of the earplug 100 and the outer portion 120, which may extend from the eartip portion 160 to the distal end region 111 of the earplug 100. An exploded view of the earplug 100 of FIG. 4 depicts each of the inner portion 140, the outer portion 120, the filter portion 180, and the eartip portion 160.

Figure 5:
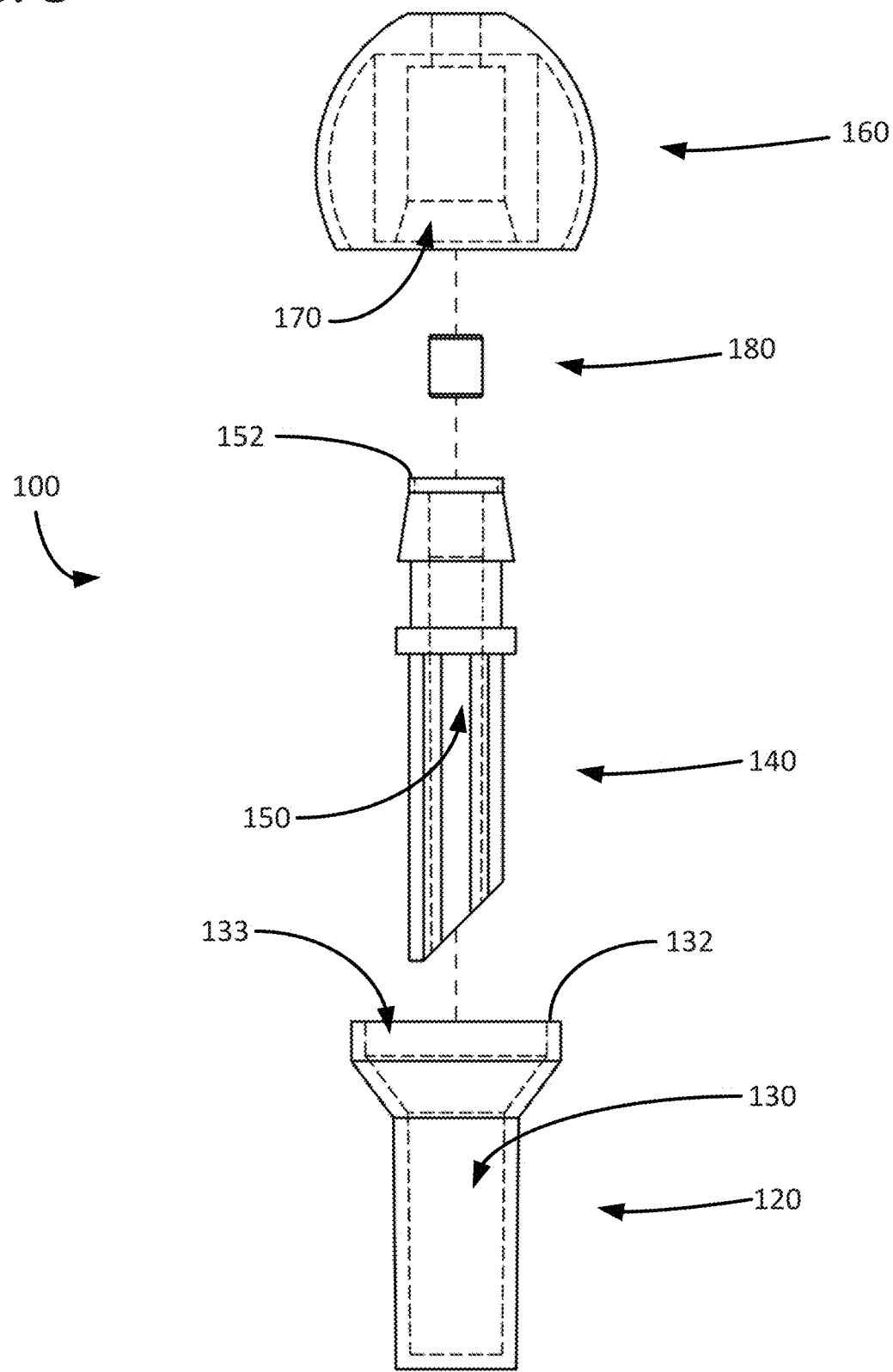
FIG. 5 is an exploded front view of the earplug of FIGS. 1-4 with the hidden, interior structure depicted using dashed lines.

As shown, the outer portion 120 may extend from a first end region 121 that corresponds to the distal end region 111 of the earplug 100 to a second end region 122 and may define an interior space 130 (e.g., as illustrated in FIG. 5) within which at least a portion of the inner portion 140 may be located and/or coupled. The inner portion 140 may also extend from a first end region 141 located proximate the first end region 121 of the outer portion 120 to a second end region 142 that may extend beyond to the second end region 122 of the outer portion 120 to a location proximate the proximal end region 112 of the earplug 100.

Figure 3:
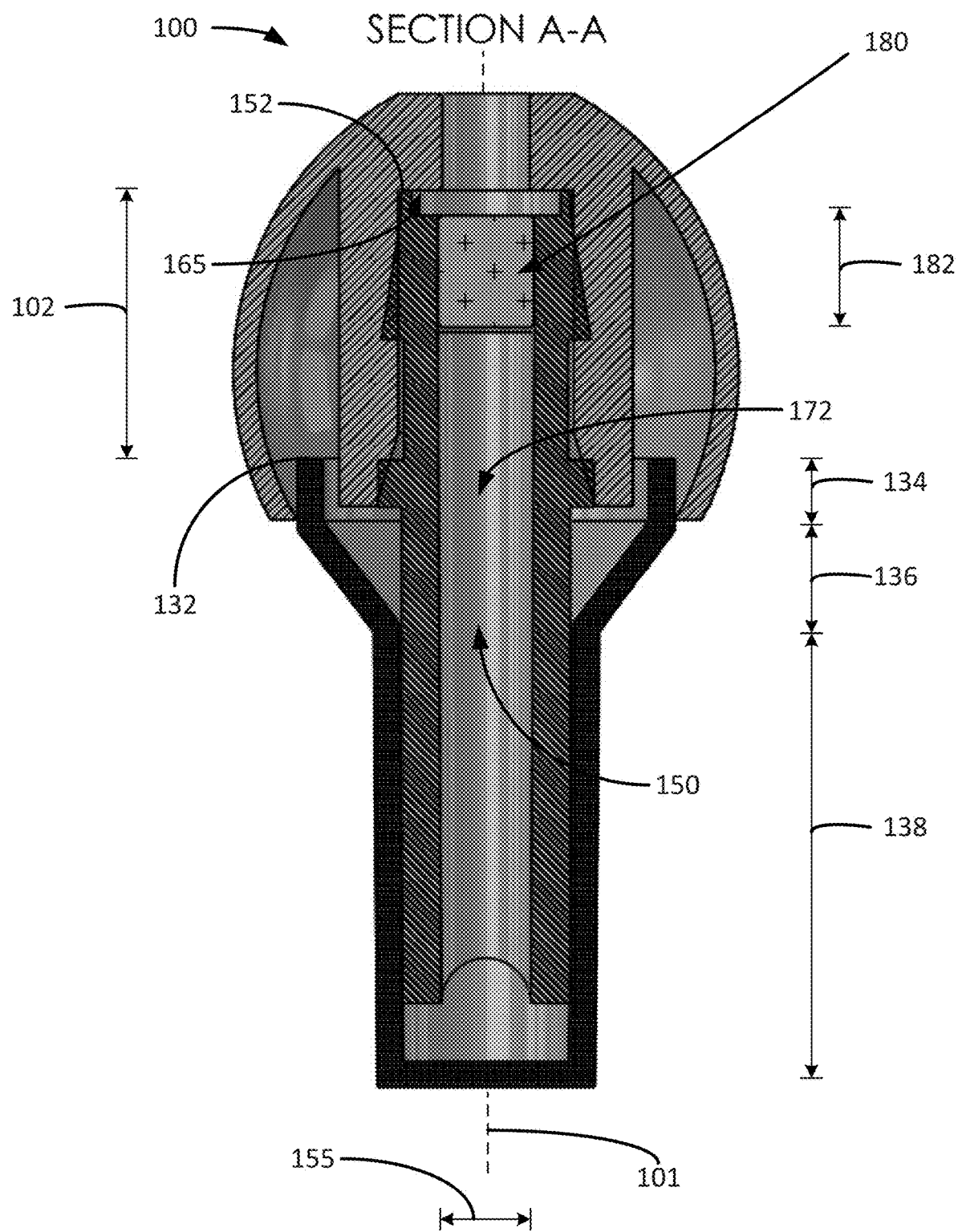
FIG. 3 is a cross-sectional view of the earplug of FIGS. 1-2 taken across line A-A.

The inner portion 140 may be substantially similar to the hollow support tube described in U.S. Pat. No. 5,113,967 entitled "Audibility Earplug" issued on May 19, 1992, which is incorporated by reference herein in its entirety. The inner portion 140 may define an aperture 150 (e.g., as illustrated in FIGS. 3 and 5) extending through the inner portion 140 from the first end region 141 to the second end region 142. The filter portion 180 may be located in the aperture 150 proximate the second end region 142 of the inner portion 140. In one or more embodiments, the filter portion 180 may be configured to help dampen the sound passing through the inner portion 140, e.g., from the external environment to the ear canal. The filter portion 180 may include anything suitable to dampen sound waves. For example, in one or more embodiments, the filter portion 180 may be similar to or the same as is described in U.S. Pat. No. 3,930,560 entitled, "Damping Element" and issued on Jan. 6, 1976, or, alternatively, described and commercially available from Knowles Electronics as the metal barreled 3300 Ohm BF-1922 damper or as the fused-mesh-only 3300 Ohm BF-3036 damper.

The outer portion 120 may be substantially similar to the cap described in U.S. Pat. No. 5,113,967 entitled "Audibility Earplug" issued on May 19, 1992, which incorporated by reference herein in its entirety. The outer portion 120 of the exemplary earplug, however, is different from the cap described in U.S. Pat. No. 5,113,967, and the differences between the outer portion 120 of the exemplary earplug 100 and the cap described in U.S. Pat. No. 5,113,967 may be provide various advantages. In one or more embodiments, at least a portion of the inner portion 140 may be coupled to the outer portion 120. The inner portion 140 and outer portion 120 coupled together may be described as a folded horn of the earplug 100.

Figure 2:
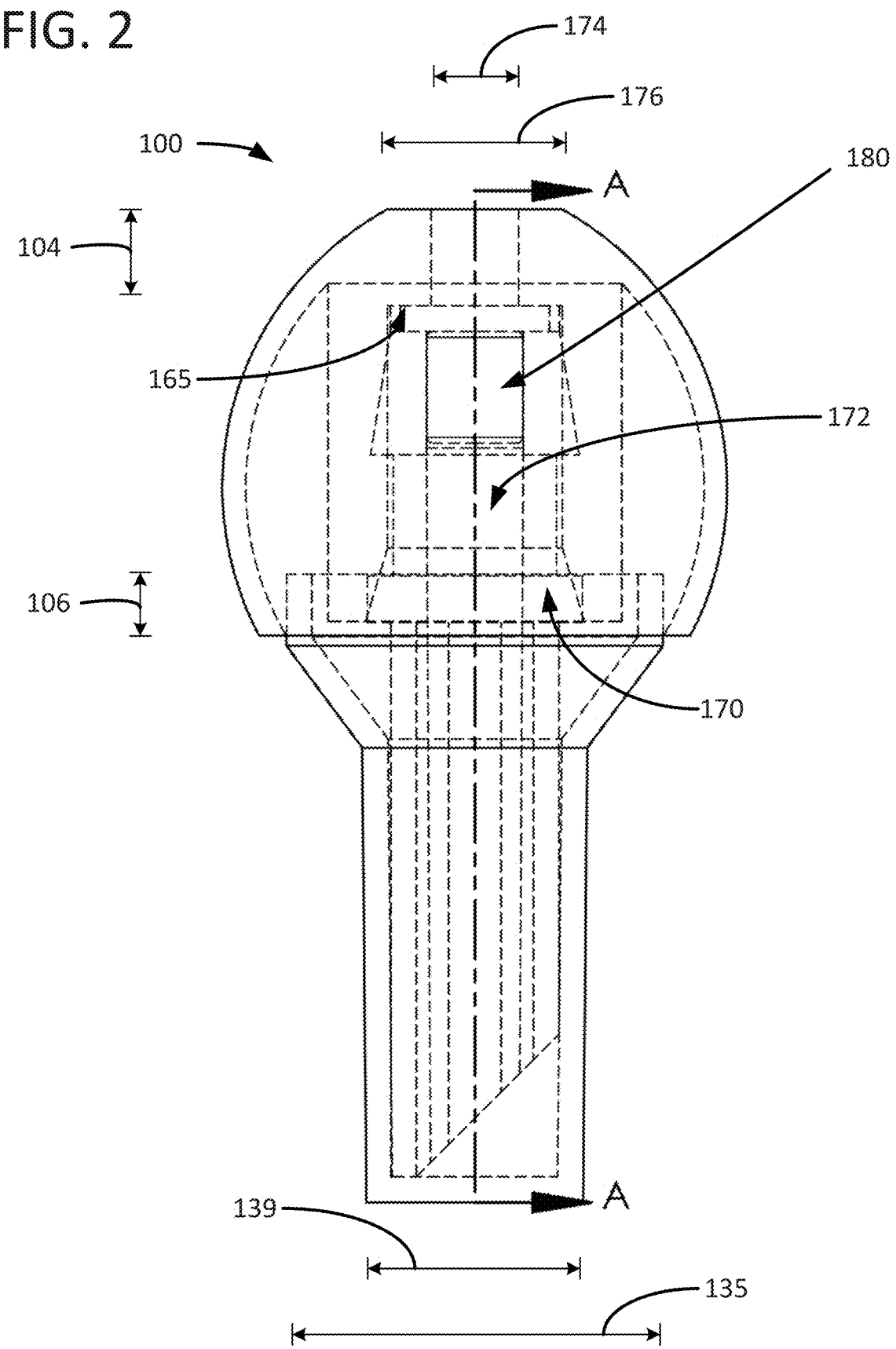
FIG. 2 is a front view of the earplug of FIG. 1 with the hidden, interior structure depicted using dashed lines.

For example, the outer portion 120 may define a length 123 from the first end region 121 to the second end region 122, and the length 123 of the outer portion 120 may be less than the length of the cap described in U.S. Pat. No. 5,113,967. More specifically, the outer portion 120 may include a proximal portion 124 extending from the second end region 122, a distal portion 128 extending from the first end region 121, and slant, or horn, portion 126 extending between the proximal and distal portions 124, 128. The proximal portion 124 may define an outer surface that extends parallel to the earplug axis 101 between and terminating at the outer portion second end and the slant portion 126. The proximal portion 124 may define a different diameter than the distal portion 128, and the slant portion 126 may having a varying diameter to extend between each of the proximal and distal portions 124, 128. For example, as shown in FIG. 2, the proximal portion 124 may define a diameter 135 that is larger than a diameter 139 defined by the distal region 128. In this example, the length 134 of the proximal portion 124 may be shorter than the length of a similar or equivalent portion of the cap described in U.S. Pat. No. 5,113,967.

In one or more embodiments, a distance 102 (e.g., as shown in FIG. 3) between an end 152 of the inner portion 140 proximate the second end region 142 of the inner portion 140 and an end 132 of the outer portion 120 proximate the second end region 122 of the outer portion 120 may be greater than a length 134 of the proximal portion 124 of the outer portion 120 measured along the earplug axis 101. In one or more embodiments, the length 134 of the proximal portion 124 of the outer portion 120 may be less than a diameter 155 of the aperture 150 of the inner portion 140 measured perpendicular to the earplug axis 101. In one or more embodiments, the length 134 of the proximal portion 124 of the outer portion 120 may be less than half of a length 138 of the distal portion 128 of the outer portion 120 measured along the earplug axis 101. In one or more embodiments, the distance 102 between the end 152 of the inner portion 140 proximate the second end region 142 of the inner portion 140 and the end 132 of the outer portion 120 proximate the second end region 122 of the outer portion 120 may be greater than a quarter of the length 138 of the distal portion 128 of the outer portion 120 measured along the earplug axis 101.

In one or more embodiments, the length 134 of the proximal portion 124 of the outer portion 120 and a length 136 of the slant portion 126 of the outer portion 120 measured along the earplug axis 101 combined may be less than the length 138 of the distal portion 128 of the outer portion 120 measured along the earplug axis 101. In one or more embodiments, the length 134 of the proximal portion 124 of the outer portion 120 may be less than a length 182 of the filter portion 180 measured along the earplug axis 101.

The shortened proximal portion 124 of the outer portion 120 of the exemplary earplug 100 may allow shorter eartip portions 160 to be used in the exemplary earplug 100, which may allow the sound channel extending from outside of ear canal of a user when using the exemplary earplug 100 through the earplug 100 into the ear canal of the user to be shorter than the earplug described in U.S. Pat. No. 5,113,967 (e.g., due to the length of the cap of the earplug described in U.S. Pat. No. 5,113,967, shorter eartip portions cannot be used since the cap portion will impinge on a user's ear canal causing discomfort, pain, etc.). In other words, the outer portion length 123, or size, may be described as being designed to allow proper comfort and fit when an exemplary eartip portion 160 is attached (e.g., the dimension of the outer portion 120 may allow proper compression of the eartip portion 160 within the outer ear canal of a user). For example, in one or more embodiments, the eartip portion 160 may be removably coupled directly to the second end of the inner portion 140.

In one more embodiments, it may be described that the earplug 100 forms a sound passage from the external environment to the ear canal. For example, sound waves may pass from the opening 133 of the outer portion 120 proximate the second end region 122 of the outer portion 120 into the interior space 130 of the outer portion 120. As such, a diameter of the inner portion 140 may be smaller than a diameter of the opening 133 at the outer portion second end such that the inner portion 140 is spaced away from the outer portion 120 at the outer portion second end to define a void therebetween. Sound waves may then travel between the inner and outer portions 140, 120 towards the first end regions 141, 121 of the inner and outer portions 140, 120. Sound waves may then pass through the aperture 150 extending from the first end region 141 to the second end region 142 of the inner portion 140, and thereafter, through the passage 172 of the eartip portion 160 (e.g. from the first end region 161 of the eartip portion 160 to the second end region 162 of the eartip portion 160) towards the ear canal.

The eartip portion 160 of the exemplary earplug 100 shown in FIGS. 1-4 may define a length 164 (as labeled in FIG. 4) from a second end region 162 corresponding to the proximal end region 112 of the earplug 100 (e.g., proximate the ear when the earplug is inserted into the ear) to a first end region 161. As shown, in FIGS. 2-4, the first end region 161 of the eartip portion 160 may overlap and extend beyond at least portions, or sections, of the second end regions 122, 142 of outer and inner portions 120, 140.

As shown in FIGS. 2-3, the eartip portion 160 may define an interior space 170 including a passage 172 from the first end region 161 to the second end region 162. The passage 172 may define two or more different diameters to provide one or more advantages. For example, the diameter 174 of the passage 172 closer to the second end region 162 of the eartip portion 160 may be smaller than the diameter 176 of the passage 172 closer to the first end region 161 of eartip portion 160, and where the two different diameters of the passage 172 meet may be defined, or described as a shelf region 165 (e.g., a surface that extends perpendicular to the passage 172 or axis extending therethrough). The shelf region 165 may be configured to restrict the eartip portion 160 from sliding, or being positioned, too far along the inner portion 140. For example, the shelf region 165 may be configured to abut, or contact, the second end region 142 of the inner portion 140 to restrict movement of the eartip portion 160 towards the distal end region 111.

In other words, the eartip portion 160 may define, or include, a "shelf" 165 at the top of the eartip portion 160 designed in such a way to act as a stopper or "shelf" 165 from the eartip portion 160 sliding down too far on the inner portion 140 protruding past the eartip portion 160. This may allow for proper placement of the eartip portion 160 and may restrict the inner portion 140 from contacting, or touching, the inner ear or ear canal of a user.

Further, smaller diameter 174 of the passage 172 closer to the second end region 162 of the eartip portion 160 and proximal end region 112 of the earplug 100 may be sized to be smaller than the diameter of the filter portion 180, which may, e.g., restrict the filter portion 180 from moving, or traversing, through the passage 172 out of the second end region 162 of eartip portion 160 into a user's ear canal if the filter portion 180 became dislodged or uncoupled from the inner portion 140. In other words, the hole at the top of the eartip portion 160 may have, or define, a specific inner diameter that is slightly smaller than the acoustic filter, which may negate limit the movement of the filter, if it were to become dislodged, into the ear canal.

The shelf region 165 may also define a thickness that creates the proper depth that the eartip portion 160 extends into the outer ear canal of a user, which may, e.g., affect sound as the sound enters the ear and may act as a continuation of the sound channel. Further, the depth may be described as being designed to create a minimal appearance of the earplug when worn by the end user, creating a virtually invisible appearance.

Further, one or more features and elements described herein, when used alone or in combination with others, may be configured to locate the second end region 142 of the inner portion 140 closer to a user's ear canal (e.g., further within, etc.) when the exemplary earplug 100 is worn by a user than other earplug designs, which may provide different and/or improved sound characteristics and/or properties for the user. For example, the shorter proximal portion 124, the eartip portion 160 design, the shelf region 165 of the eartip portion 160, and other features may be used to locate the second end region 142 of the inner portion 140 closer to a user's ear canal.

For example, Table 1 below illustrates basic attenuation data, e.g., the decibel reduction at various Frequencies for the exemplary earplug 100 described herein and other earplug designs. Earplugs as described herein were tested according to ANSI 53.19-1974 test methods. The other earplugs identified in Table 1 may be the same or similar to the ER20 made by Etymōtic®. As shown in Table 1 below, the earplugs described herein provide a greater decibel reduction at each frequency than the other earplugs. This decibel reduction (e.g., across a range of frequencies) may be used to determine a Noise Reduction Rating (NRR) for a given product. A higher NRR may reflect a greater degree of hearing protection as provided by the Earplugs described herein, as compared to the other earplugs.

TABLE 1

Decibel reduction at various frequencies.

| | Frequency (Hz) | | | | | | | |
|---|---|---|---|---|---|---|---|---|
| | 125 | 250 | 500 | 1000 | 2000 | 4000 | 8000 | NRR |
| Other Earplugs | 13.2 | 15.3 | 16.7 | 18.3 | 20.8 | 18.3 | 21.6 | 12 |
| Earplugs described herein | 16.4 | 15.8 | 19.2 | 22.6 | 26.9 | 27.2 | 29.7 | 15 |

A greater hearing protection or decibel level reduction may also be achieved relatively equally across the frequencies which means that the sound which reaches the ears approximates the actual sound that is being produced. As compared to foam earplugs, different frequencies may be damped differently, resulting in, e.g., higher frequencies being more distorted or muffled because the foam earplug is design to block sound. On the other hand, the earplugs described herein may provide added sound clarity dampening of all frequencies, and therefore, allowing the higher frequencies carrying speech and music to come through clearly along with lower frequencies.

Additionally, it may be described that the distance from the filter portion 180 and/or second end region 142 of the inner portion 140 to the second end region 162 of the eartip portion 160 and/or end opening of the eartip portion 160 may define a sound channel length 104 (e.g., as shown in FIG. 2). In the exemplary earplugs 100 described herein, the sound channel length 104 may be shorter than other earplugs, which may provide different and/or improved sound characteristics and/or properties for the user. Also, the sound channel length 104 may be greater than a distance 106 (e.g., as shown in FIG. 2) that the outer portion 120 extends within the interior space 170 of the eartip portion 160.

Figure 6A:
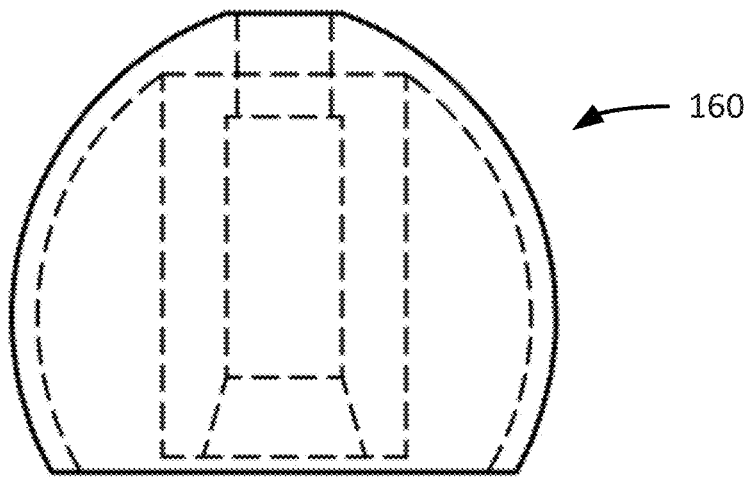
FIG. 6A is a front view of an exemplary eartip portion of the earplug of FIGS. 1-5 with the hidden, interior structure depicted using dashed lines.
Figure 6B:
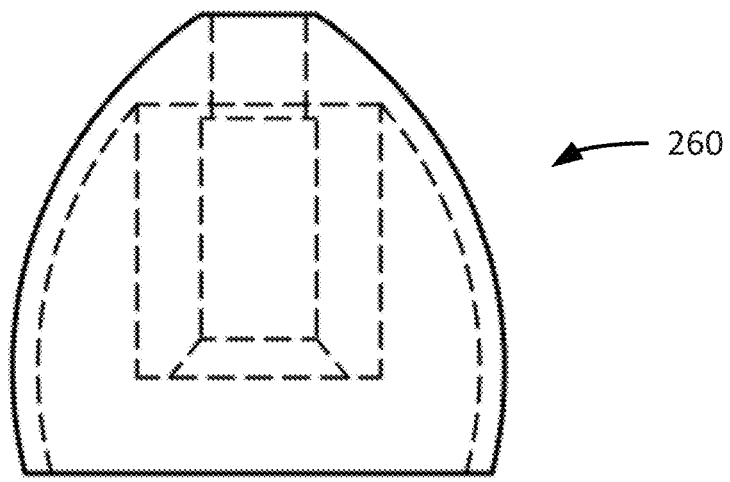
FIG. 6B is a front view of another exemplary eartip portion for use with exemplary earplugs with the hidden, interior structure depicted using dashed lines.
Figure 6C:
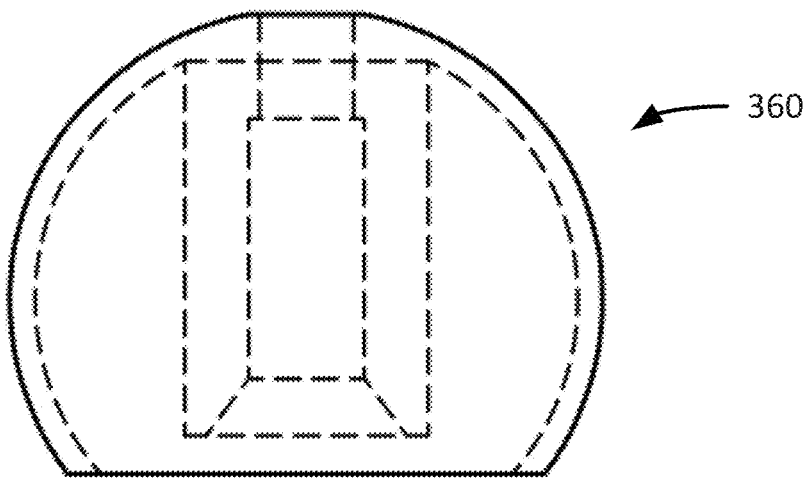
FIG. 6C is a front view of another exemplary eartip portion for use with exemplary earplugs with the hidden, interior structure depicted using dashed lines.
Figure 7:
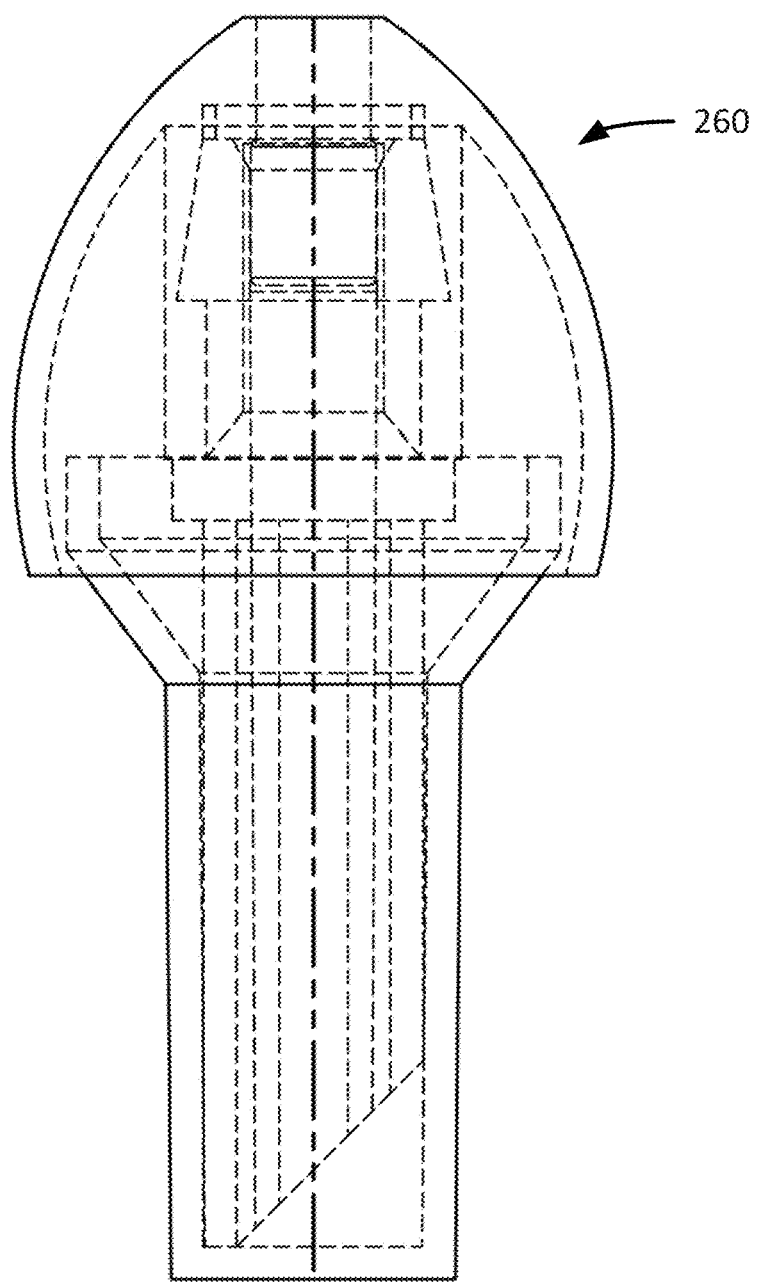
FIG. 7 is a front view of an exemplary earplug using the eartip portion of FIG. 6B with the hidden, interior structure depicted using dashed lines.
Figure 8:
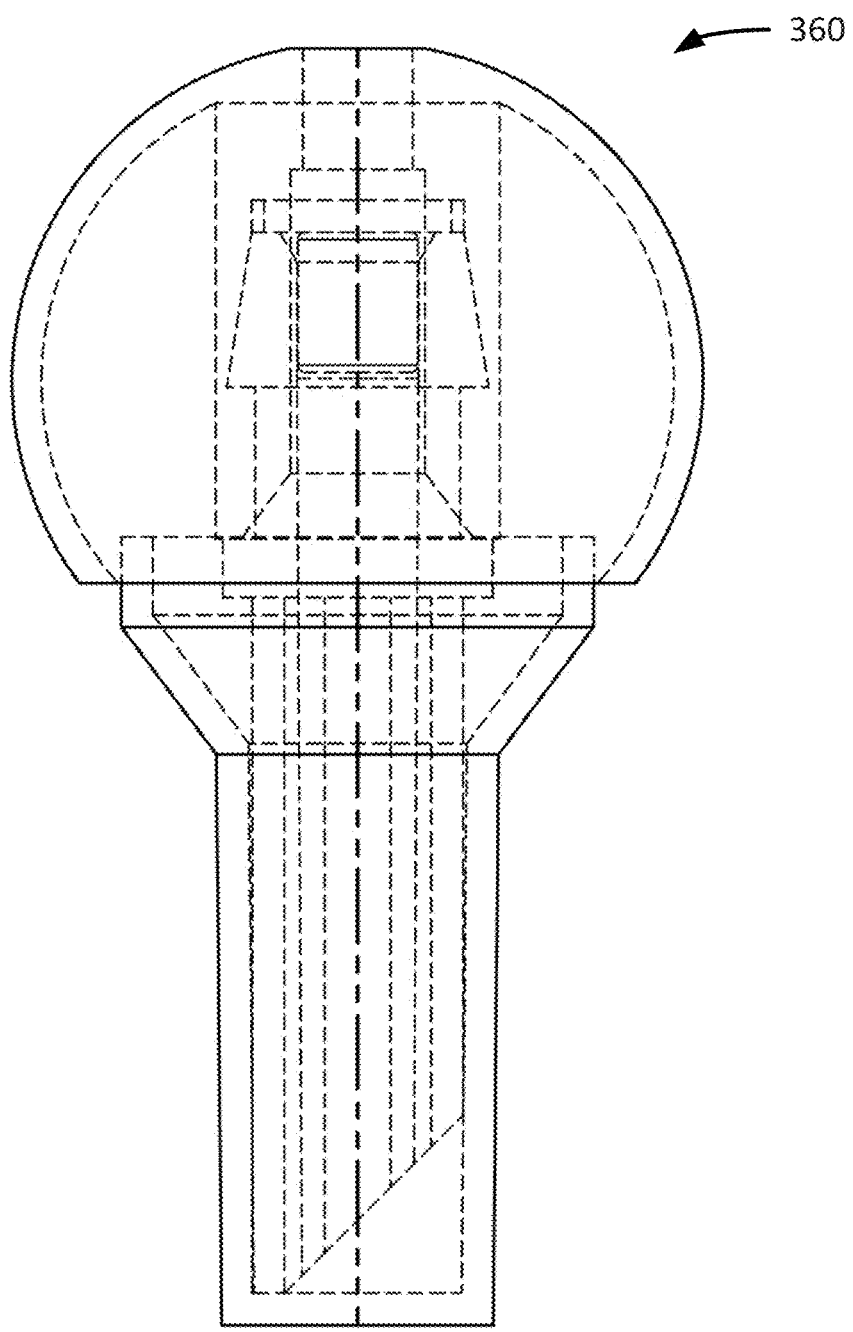
FIG. 8 is a front view of an exemplary earplug using the eartip portion of FIG. 6C with the hidden, interior structure depicted using dashed lines.

Various different eartip portions may be used in for the earplug described herein, while still providing the same advantages. For example, FIGS. 6A-6C illustrate various eartip portions that may be used in connection with the inner and outer portions illustrated in FIGS. 1-5. Specifically, FIG. 6A illustrates the eartip portion 160 of the earplug 100 of FIGS. 1-5, FIG. 6B illustrates another eartip portion 260 for use with exemplary earplugs, and FIG. 6C illustrates yet another eartip portion 360 for use with exemplary earplugs. Further, FIG. 7 illustrates the eartip portion 260 from FIG. 6B coupled or attached to the exemplary earplug and FIG. 8 illustrates the eartip portion 360 from FIG. 6C coupled or attached to the exemplary earplug. Each of FIGS. 6A-6C, 7, and 8 illustrates hidden, interior structure using dashed lines.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed:

1. An earplug extending along an earplug axis from a distal end to a proximal end, wherein the earplug comprises:
   an outer portion extending between an outer portion first end and an outer portion second end, wherein the outer portion first end corresponds to the distal end of the earplug, and wherein the outer portion comprises:
      a proximal portion extending from the outer portion second end,
      a distal portion extending from the outer portion first end, and
      a slant portion between the proximal portion and the distal portion,
      wherein the outer portion defines an interior space and an opening at the outer portion second end extending into the interior space, wherein an outer surface of the proximal portion extends parallel to the earplug axis between and terminating at the outer portion second end and the slant portion; and
   an inner portion extending between an inner portion first end and an inner portion second end, wherein the proximal end of the earplug is closer to the inner portion second end than the inner portion first end, wherein at least a portion of the inner portion is coupled to the outer portion and at least the inner portion first end is located within the interior space of the distal portion of the outer portion, wherein at least the inner portion second end is located outside of the outer portion, wherein the inner portion defines an aperture extending between the inner portion first end and the inner portion second end,
   wherein a distance between the inner portion second end and the outer portion second end is greater than a length of the proximal portion of the outer portion measured along the earplug axis.

2. The earplug of claim 1, wherein the length of the proximal portion of the outer portion is less than a diameter of the aperture of the inner portion measured perpendicular to the earplug axis.

3. The earplug of claim 1, wherein the length of the proximal portion of the outer portion is less than half of a length of the distal portion of the outer portion measured along the earplug axis.

4. The earplug of claim 1, wherein the distance between the inner portion second end and the outer portion second end is greater than a quarter of a length of the distal portion of the outer portion measured along the earplug axis.

5. The earplug of claim 1, wherein the length of the proximal portion of the outer portion and a length of the slant portion of the outer portion measured along the earplug axis combined is less than a length of the distal portion of the outer portion measured along the earplug axis.

6. The earplug of claim 1, further comprising a filter portion located in the aperture of the inner portion.

7. The earplug of claim 6, wherein the length of the proximal portion of the outer portion is less than a length of the filter portion measured along the earplug axis.

8. The earplug of claim 1, further comprising an eartip portion removably coupled to the inner portion second end and configured to be positioned in an ear canal, wherein the eartip portion extends between an eartip portion first end and an eartip portion second end and defines an interior space, wherein the inner portion second end is within the interior space of the eartip portion.

9. The earplug of claim 8, wherein the outer portion second end is within the interior space of the eartip portion proximate the eartip portion first end.

10. The earplug of claim 1, wherein the proximal portion of the outer portion defines a diameter greater than a diameter of the distal portion of the outer portion, wherein the diameters of the proximal portion and distal portion are measured perpendicular to the earplug axis.

11. The earplug of claim 10, wherein the slant portion defines a varying diameter extending between the proximal portion and the distal portion, wherein the diameter of the slant portion is measured perpendicular to the earplug axis.

12. An earplug extending along an earplug axis from a distal end to a proximal end, wherein the earplug comprises:
   an outer portion extending between an outer portion first end and an outer portion second end, wherein the outer portion defines an interior space and an opening at the outer portion second end extending into the interior space;
   an inner portion extending between an inner portion first end and an inner portion second end, wherein at least a portion of the inner portion is coupled to the outer portion and the inner portion first end is located within the interior space of the outer portion, wherein the inner portion defines an aperture extending between the inner portion first end and the inner portion second end;
   a filter portion located in the aperture of the inner portion;
   an eartip portion removably coupled directly to the second end of the inner portion second end and configured to be positioned in an ear canal, wherein the eartip portion extends between an eartip portion first end and an eartip portion second end and defines an interior space, wherein the inner portion second end is within the interior space of the eartip portion, wherein the outer portion second end is within the interior space of the eartip portion, and wherein the outer portion second end is closer to the eartip portion first end than the eartip portion second end, wherein the eartip portion second end corresponds to the proximal end of the earplug, wherein a distance between the inner portion second end and the eartip portion second end is greater than a distance that the outer portion extends within the interior space of the eartip portion.

13. The earplug of claim 12, wherein the eartip portion contacts an outer surface of the outer portion.

14. The earplug of claim 12, wherein the filter portion is located proximate the inner portion second end.

15. The earplug of claim 12, wherein the interior space of the eartip portion defines a passage extending between the eartip portion first end and the eartip portion second end, wherein at least a portion of the inner portion extends within at least a portion of the passage of the eartip portion.

16. The earplug of claim 15, wherein a diameter of the passage of the eartip portion proximate the eartip portion second end is less than a diameter of the at least a portion of the passage that receives the inner portion, wherein the inner portion defines a diameter such that the inner portion is restricted from passing through the passage of the eartip portion proximate the eartip portion second end.

17. The earplug of claim 12, wherein the inner portion second end is closer to the eartip portion second end than the eartip portion first end.

* * * * *

UNITED STATES PATENT AND TRADEMARK OFFICE
CERTIFICATE OF CORRECTION

PATENT NO. : 11,324,637 B2
APPLICATION NO. : 15/344920
DATED : May 10, 2022
INVENTOR(S) : Jackson Robert Mann It is certified that error appears in the above-identified patent and that said Letters Patent is hereby corrected as shown below:

In the Claims

In Column 10, Lines 9-10 (Claim 12), "the second end of" should be deleted.

Signed and Sealed this
Twenty-sixth Day of July, 2022

Katherine Kelly Vidal
*Director of the United States Patent and Trademark Office*